United States Patent
Wu

(10) Patent No.: US 9,283,434 B1
(45) Date of Patent: Mar. 15, 2016

(54) METHOD OF DETECTING AND PROMPTING HUMAN LOWER LIMBS STEPPING MOTION

(71) Applicant: STRENGTH MASTER FITNESS TECH CO., LTD., Changhua County (TW)

(72) Inventor: Shu Yao Wu, Taichung (TW)

(73) Assignee: Strength Master Fitness Tech Co., Ltd., Changhua County (TW)

( * ) Notice: Subject to any disclaimer, the term of this patent is extended or adjusted under 35 U.S.C. 154(b) by 0 days.

(21) Appl. No.: 14/501,329

(22) Filed: Sep. 30, 2014

(51) Int. Cl.
*A63B 24/00* (2006.01)
*A63B 22/06* (2006.01)

(52) U.S. Cl.
CPC .......... *A63B 24/0062* (2013.01); *A63B 22/0605* (2013.01)

(58) Field of Classification Search
CPC . A63B 24/00; A63B 24/0062; A63B 22/0605
IPC ............. A63B 24/00, 24/22, 2220/22, 2200/16, A63B 2220/51
See application file for complete search history.

(56) References Cited

U.S. PATENT DOCUMENTS

| | | | | |
|---|---|---|---|---|
| 5,257,540 | A * | 11/1993 | Bower | A61B 5/221 482/900 |
| 8,641,581 | B2 * | 2/2014 | Bacanovic | A63B 22/0605 482/57 |
| 2002/0072452 | A1 * | 6/2002 | Torkelson | A63B 21/1411 482/51 |
| 2005/0233285 | A1 * | 10/2005 | Miyamaru | G09B 9/058 434/61 |
| 2011/0111923 | A1 * | 5/2011 | Bacanovic | A63B 22/0605 482/8 |
| 2015/0141200 | A1 * | 5/2015 | Murray | A63B 21/154 482/5 |

* cited by examiner

*Primary Examiner* — Glenn Richman
(74) *Attorney, Agent, or Firm* — Rosenberg, Klein & Lee

(57) ABSTRACT

A method of detecting and prompting a human lower limbs stepping motion is applied to an exercise machine with pedals installed to both left and right sides of the exercise machine and provided for detecting a pedaling force while stepping the pedals. In the method, a force sensor is installed to the pedals, such that when an exerciser steps on the pedals by feet alternately, the force sensor detects, generates and transmits an electric signal to a control unit and converts the electric signal into a pedaling force value, and the control unit compares the pedaling force value with a predetermined value and prompts a message when the pedaling force value is beyond the range of the predetermined value.

17 Claims, 17 Drawing Sheets

METHOD OF DETECTING AND PROMPTING HUMAN LOWER LIMBS STEPPING MOTION

FIELD OF THE INVENTION

The present invention relates to a method of detecting and prompting a human lower limbs stepping motion, in particular to the method capable of detecting a human lower limbs stepping motion, and timely providing a message to prevent exercise injury.

BACKGROUND OF THE INVENTION

With reference to FIG. 17 for a conventional exercise machine, the exercise machine is a fitness bike, and the fitness bike comprises a bike body 91, two pedals 92 symmetrically installed to both left and right sides of the bike body 91 respectively, such that exerciser may place their feet on the pedals 92 and step on the pedals 92 alternately to achieve a lower limbs stepping motion for exercise. Other exercise machines such as steppers also have the pedals 92 installed to both sides of the steppers.

However, the aforementioned conventional exercise machines do not have the function of detecting a stepping posture or measuring a pedaling force, so that if the exerciser's stepping posture or pedaling force is improper during the process of using the exercise machines, there is no way to inform the exercisers to make corrections immediately, and the exercisers can only find out the problem after a certain part of their body has pains. Although the exercisers can make improvements later, yet the exercisers may have sports injuries which may harm their health.

SUMMARY OF THE INVENTION

Therefore, it is a primary objective of the present invention to overcome the aforementioned problem of the prior art by providing a method of detecting and prompting a human lower limbs stepping motion, so that a message may be prompted immediately to alert any improper stepping posture or pedaling force, so as to prevent sports injuries during the stepping motion.

To achieve the aforementioned objective, the present invention provides a method of detecting and prompting a human lower limbs stepping motion, and the method is applied in an exercise machine with pedals installed to both left and right sides of the exercise machine respectively for detecting a pedaling force when an exerciser steps on the pedals, and the method comprises the steps of: installing at least one force sensor to each pedal for detecting the pedaling force; detecting the pedaling force by the at least one force sensor installed to each pedal to generate at least one electric signal when the feet of the exerciser's legs step on the pedals on both left and right sides of the exercise machine; transmitting the at least one electric signal to a control unit and converting the electric signal into a pedaling force value; comparing whether the pedaling force value or a difference value of the pedaling force values detected by the at least one force sensor is equal to a predetermined value installed in the control unit by the control unit; and prompting a message if the pedaling force value or the difference value of the pedaling force values detected by the at least one force sensor is not equal to the predetermined value.

Wherein, the pedaling force value is the sum of the pedaling force values detected by at least one force sensor of each pedal, and the pedaling force value of each pedal is compared with the predetermined value of the control unit separately to determine whether the sum of the pedaling force values of each pedal is equal to the predetermined value, and a message will be prompted if the sum is not equal to the predetermined value.

Wherein, the method further comprises the steps of: calculating a difference value of the pedaling force values by the control unit when the exerciser steps on the two pedals alternately; calculating a difference value of the sum of the pedaling force values of each pedal by the control unit when the exerciser steps on the two pedals alternately; and prompting a message, if the difference value is not equal to the predetermined difference value.

Wherein, each pedal includes at least one front force sensor installed to the front of the pedal and at least one rear force sensor installed to the rear of the pedal, and the control unit compares whether the difference value of the pedaling forces detected by the at least one front force sensor and at least one rear force sensor is equal to the predetermined difference value, and a message is prompted if the difference value is not equal to the predetermined difference value.

Wherein, each pedal includes at least one left force sensor installed to the left side of the pedal and at least one right force sensor installed to the right side of the pedal, and the control unit compares whether a difference value of the pedaling forces detected by the at least one left force sensor and the at least one right force sensor is equal to the difference value of the pedaling forces detected by the force sensors, and a message will be prompted if the difference value is not equal to the difference values of the pedaling forces detected by the force sensors.

Wherein, each pedal is coupled to a wheel pivotally installed in the exercise machine, and an angle detector is installed at the wheel, and the wheel has a detecting portion corresponsive to the angle detector, and an exerciser may step on the pedals reciprocally by the feet, and the angle detector is provided for detecting a position signal of a rotation angle of the wheel, and the control unit uses the position signal to calculate the position of the exerciser's foot.

DESCRIPTION OF THE PREFERRED EMBODIMENTS

With reference to FIGS. 1 to 16 for the method of detecting and prompting a human lower limbs motion in accordance with the present invention, the invention will become clearer in light of the following detailed description of an illustrative embodiment of this invention described in connection with the drawings. It is intended that the embodiments and drawings disclosed herein are to be considered illustrative rather than restrictive.

The present invention provides a method of detecting and prompting a human lower limbs stepping motion, and the method is applied in an exercise machine with pedals installed to both left and right sides of the exercise machine respectively, and the exercise machine includes a resistance device for providing a resistance when the exerciser steps on the pedals, and detects a pedaling force when the exerciser steps on the pedals. This method comprises the steps of: installing at least one force sensor to each pedal for detecting a pedaling force; generating an electric signal through the detection by the force sensor of each pedal when the feet of the exerciser's feet step on the pedals on the left and right sides of the exercise machine alternately; transmitting the electric signal to a control unit and converting the electric signal into a pedaling force value; comparing whether the pedaling force value is equal to a predetermined value stored in the control unit by the control unit; and prompting a message if the pedaling force value is not equal to the predetermined value.

Figure 1:
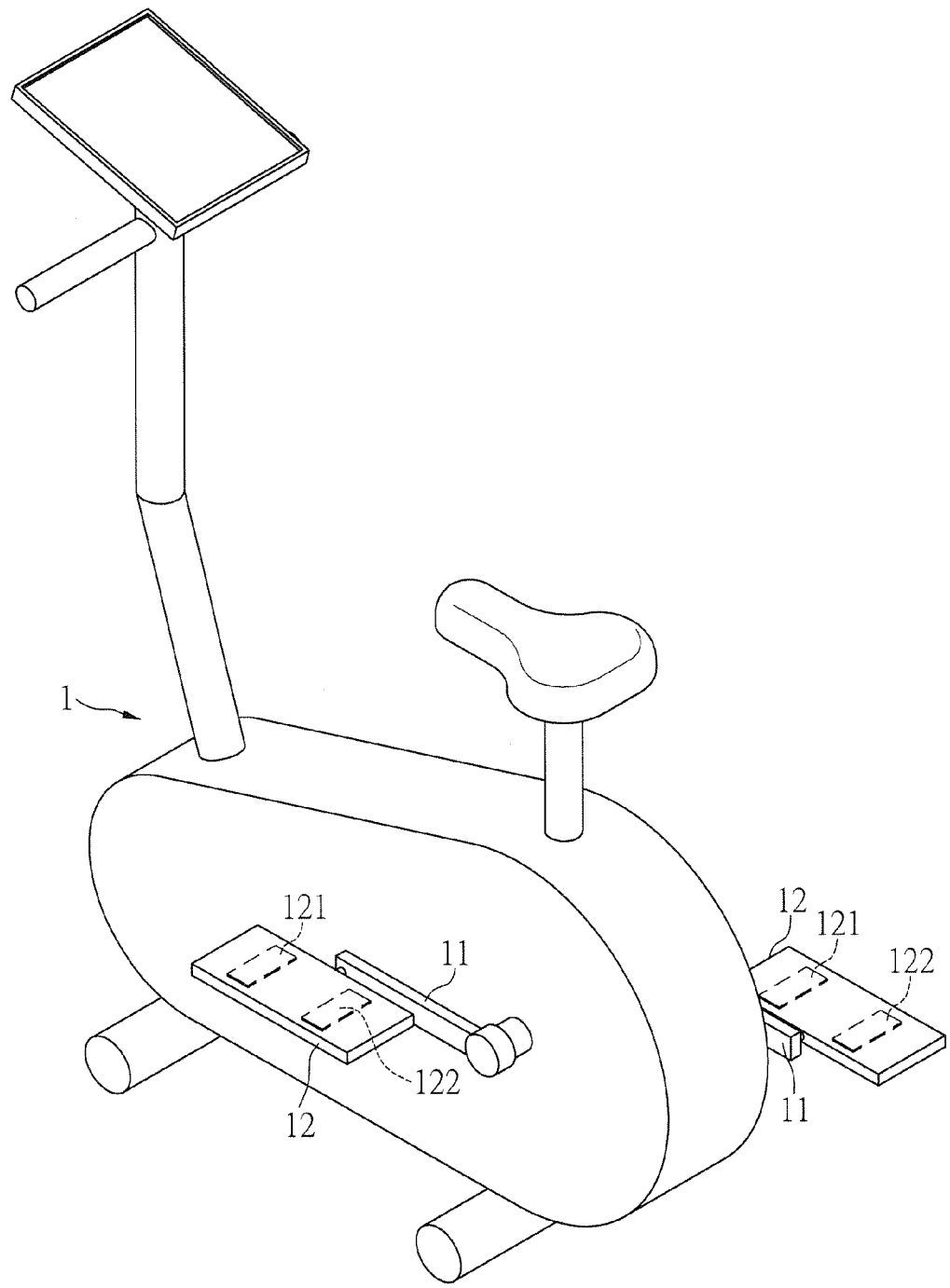
FIG. 1 is a perspective view of a fitness bike in accordance with first and second preferred embodiments of the present invention.

In FIG. 1, the exercise machine of this preferred embodiment is a fitness bike 1, and the fitness bike 1 comprises two pedals 12 pivotally installed to both left and right sides of the fitness bike 1 by a crank 11, a resistance device (not shown in the figure) installed in the fitness bike 1, so that when an exerciser rides on the fitness bike 1, the exerciser may step on the pedals on the left and right sides of the fitness bike 1 by both feet of the exerciser's legs to produce a circular motion.

Figure 2:
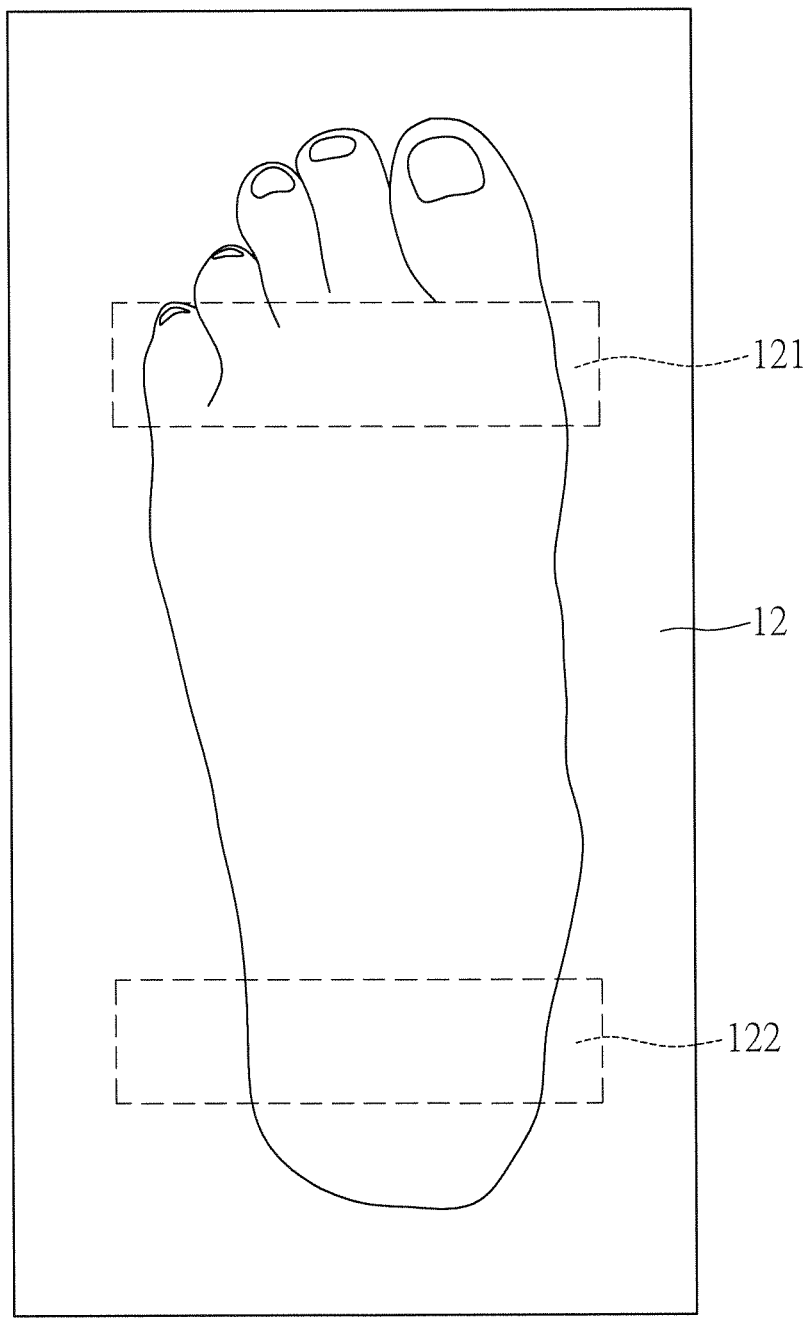
FIG. 2 is a schematic view, showing the position of a force sensor installed to a pedal in accordance with the first preferred embodiment of the present invention.
Figure 3:
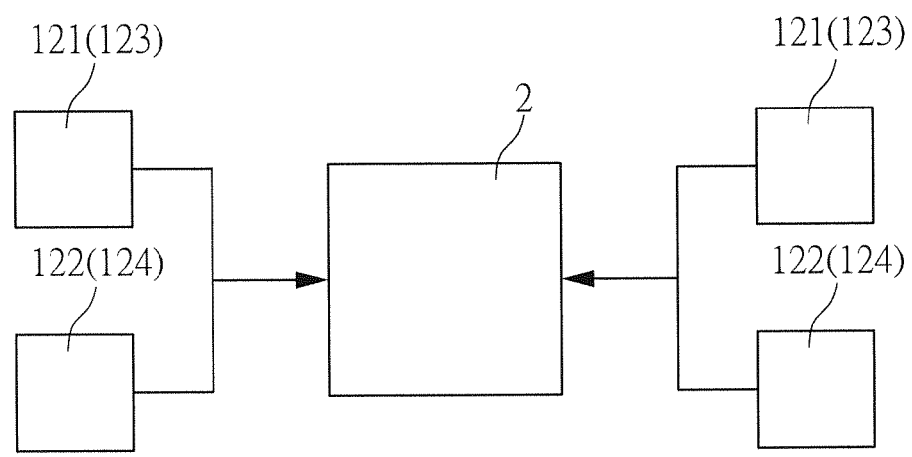
FIG. 3 is a block diagram of a force sensor electrically coupled to a control unit in accordance with the first or second preferred embodiment of the present invention.

In FIG. 2, the fitness bike 1 of this preferred embodiment further comprises a front force sensor 121 installed to the front of each pedal 12, and a rear force sensor 122 installed to the rear of each pedal 12. In FIG. 3, the front force sensor 121 and the rear force sensor 122 of each pedal 12 are electrically coupled to a control unit 2.

Figure 4:
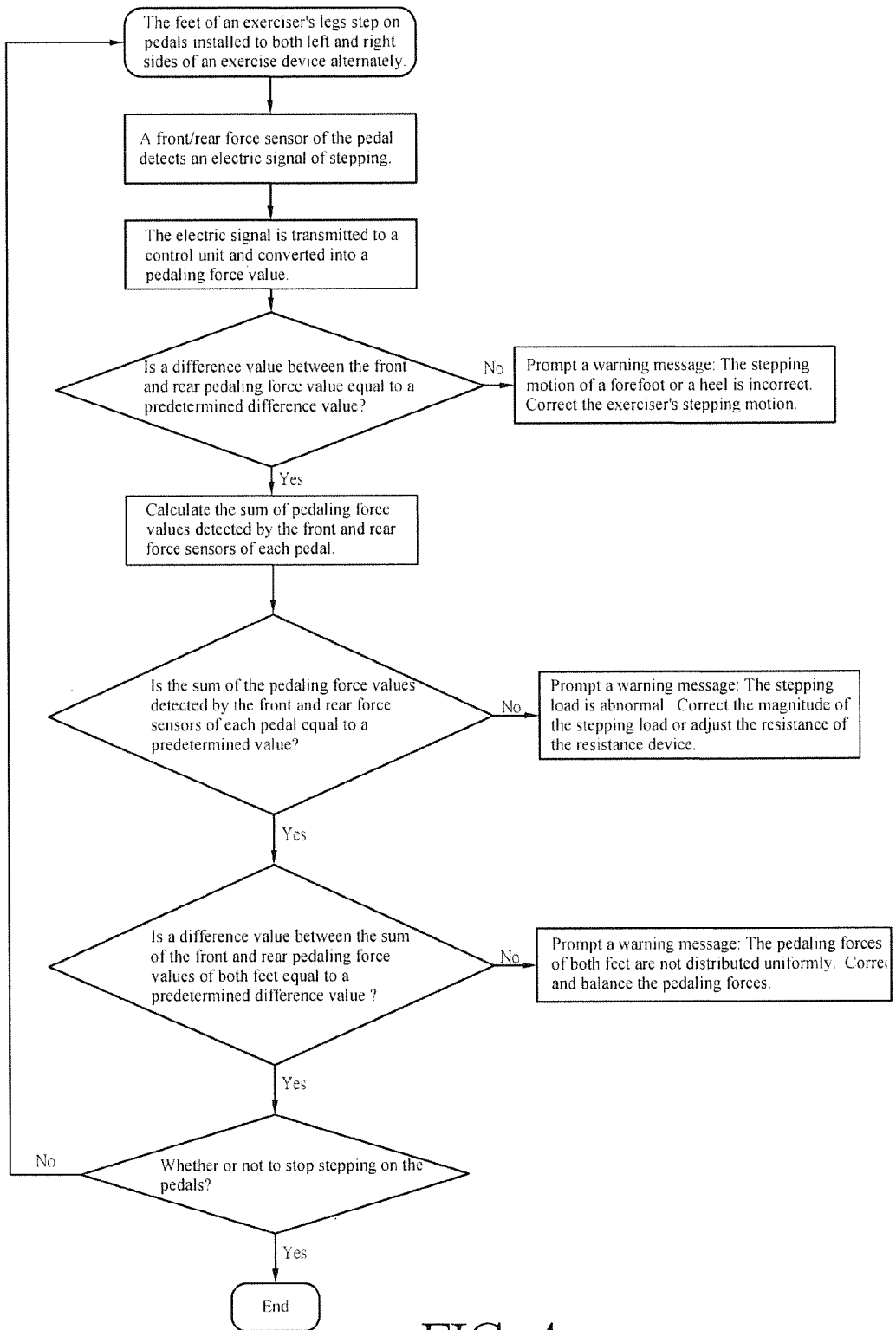
FIG. 4 is a flow chart of detecting and prompting a human lower limbs stepping motion in accordance with the first preferred embodiment of the present invention.

With reference to FIG. 4 for the flow chart of a method of detecting and prompting a human lower limbs stepping motion of this preferred embodiment, when an exerciser starts stepping on the pedals 12 on both left and right sides of the fitness bike 1 by the feet of both legs respectively, the front force sensor 121 detects a pedaling force at a forefoot position to generate an electric signal, and the rear force sensor 122 detects a force at the rear of each pedal 12 to generate another electric signal, and the front force sensor 121 and the rear force sensor 122 transmit the measured electric signals to a control unit 2 and the control unit 2 converts the electric signals into pedaling force values, and the control unit 2 further calculates whether a difference value of the pedaling forces detected by the front force sensor 121 and the rear force sensor 122 is equal to a corresponding predetermined difference value.

If the difference value of the pedaling forces detected by the front force sensor 121 and the rear force sensor 122 is not equal to a corresponding predetermined difference value, then a message will be prompted to show that the stepping motion at an exerciser's feet is incorrect and further corrects the exerciser's stepping motion. For example, if the pedaling force detected by the front force sensor 121 is lower than the corresponding predetermined value, and the pedaling force detected by the rear force sensor 122 is higher than the corresponding predetermined value, then it will be determined that the exerciser's toes point up while stepping on the pedals 12, and a message will be prompted to notice the exerciser to let the exerciser make necessary corrections and not to let the toes point up while stepping on the pedals 12.

If the difference value of the pedaling forces detected by the front force sensor 121 and the rear force sensor 122 is equal to a corresponding predetermined difference value, it will be determined that the sum of the pedaling force values of each pedal 12 is not equal to a corresponding predetermined value. Now, the pedaling force value is the sum of the pedaling force values detected by the front force sensor 121 and the rear force sensor 122 of each pedal 12, and the pedaling force value (referring to the sum of the pedaling force values) of each pedal 12 is compared with the corresponding predetermined value of the control unit 2, so as to determine whether the sum of the pedaling force values of each pedal 12 is equal to the corresponding predetermined value. If the sum of the pedaling forces is not equal to the predetermined value, then a message will be prompted to show an abnormal stepping load, and further correct the magnitude of the pedaling force or adjust the resistance provided by a resistance device. For example, when the exerciser steps on the pedals 12, the sum of the pedaling force values detected by the front force sensor 121 and the rear force sensor 122 when the exerciser's left foot steps on the pedals 12 is significantly greater than the corresponding predetermined value, a message will be prompted to indicate a too-large stepping load and request the exerciser to reduce the stepping speed or the resistance of the resistance device.

If the sum of the pedaling force values detected by the front force sensor 121 and the rear force sensor 122 is equal to the corresponding predetermined value, and the method will further determine whether the pedaling forces of the exerciser's feet are distributed uniformly. Now, the control unit calculates a difference value of the sum of the pedaling force values when the two pedals 12 are stepped alternately, and the control unit 2 has a difference value of the sum of the pedal force values stored therein and corresponsive to the predetermined difference value. The control unit 2 compares the difference value with the predetermined difference value to determine whether they are equal. If the difference value is not equal to the predetermined difference value, a message will be prompted to show that the pedaling forces of the exerciser's feet are not allocated uniformly and further revise the pedaling forces of the exerciser's feet to be uniform. For example, during the process of stepping on the pedals 12, the sum of the pedaling force values detected by the front force sensor 121 and the rear force sensor 122 of the pedal 23 when the exerciser's right foot steps on the pedal 12 is significantly greater than the sum of the pedaling force values detected by the front force sensor 121 and the rear force sensor 122 when the exerciser's left foot steps on the pedal 12, a message will be prompted to show that the right front pedaling force is greater than the left foot pedaling force and request the exerciser to reduce the pedaling force of the right foot or increase the pedaling force of the left foot to balance the pedaling force of the exerciser's feet.

If the difference value is equal to the predetermined difference value, the method will further determine whether the exerciser stops stepping on the pedal 12. If the exerciser stops stepping on the pedal 12, then the detection of human movement mechanics will end. If the exerciser continues stepping on the pedal 12, then the human movement mechanics will be detected continuously.

In summation of the description above, the present invention has the following advantages: The pedal 12 includes a force sensor (such as the aforementioned front force sensor 121 and rear force sensor 122) and the control unit 2 converts an electric signal into a pedaling force value and compares the pedaling force value with the predetermined value or the difference value of the sum of the pedal forces values stored in the control unit 2, so as to determine whether the stepping posture and pedaling force are abnormal when the exerciser steps on the pedals 12 by the feet of both legs. For example, the situations including the incorrect stepping motion of the exerciser's forefoot and heel, abnormal stepping load, and uneven pedaling forces of both legs can be determined. A message can be prompted to notice the exerciser when the comparison result is produced, so that the exerciser may correct the abnormality by adjusting the stepping posture and the pedaling force, so as to prevent sports injuries during the exercise process, and avoid harming our health.

Figure 5:
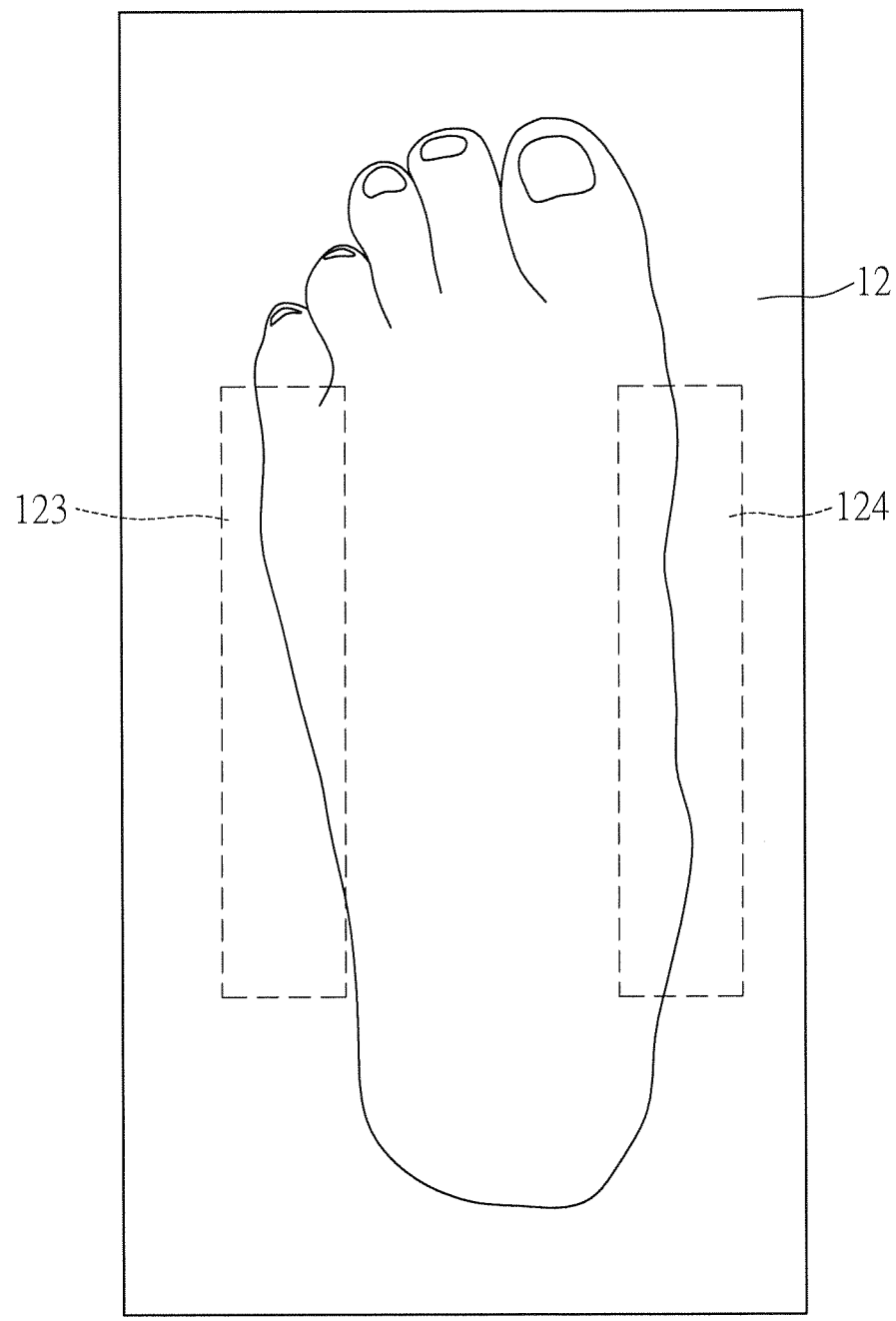
FIG. 5 is a schematic view, showing the position of a force sensor installed to a pedal in accordance with the second preferred embodiment of the present invention.

Of course, the present invention still has many other embodiments with minor changes and modifications. With reference to FIGS. 1, 3, 5 and 6 for the second preferred embodiment of the present invention, the main difference between this preferred embodiment and the first preferred embodiment resides on that each pedal 12 does not have any front force sensor 121 or rear force sensor 122, but a left force sensor 123 is installed at a stepping position on the left side of the feet and a right force sensor 124 is installed at a stepping position on the right side of the feet instead as shown in FIG. 5. In FIG. 3, the left force sensor 123 and the right force sensor 124 of each pedal 12 are electrically coupled to the control unit 2.

Figure 6:
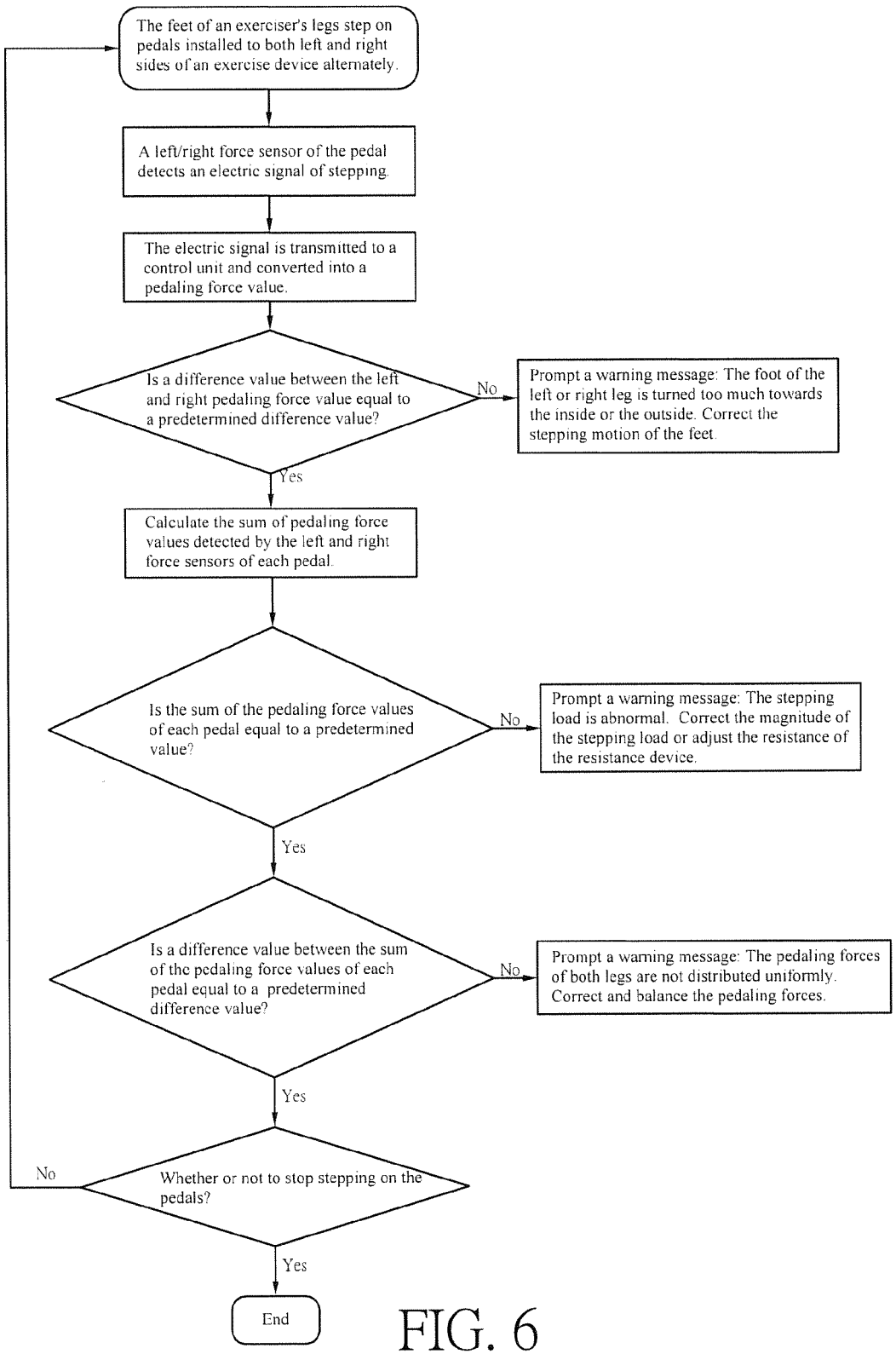
FIG. 6 is a flow chart of detecting and prompting a human lower limbs stepping motion in accordance with the second preferred embodiment of the present invention.

With reference to FIG. 6 for the flow chart of a method of detecting and prompting a human lower limbs stepping motion of this preferred embodiment, when the exerciser starts stepping on the pedal 12 installed to both left and right sides of the fitness bike 1 by the feet of both legs to produce a circular motion, the left force sensor 123 detects a pedaling force on the left side to generate an electric signal, and the right force sensor 124 detects a right pedaling force to generate another electric signal, and the left force sensor 123 and the rear force sensor 124 transmit the measured electric signals to the control unit 2, and the measured electric signals into pedaling force values, and the control unit 2 calculates a difference value of the pedaling force values detected by the left force sensor 123 and the right force sensor 124 and determines whether the difference value is equal to the corresponding predetermined difference value.

If the difference value is not equal to the corresponding predetermined difference value, a message will be prompted to indicate the uneven forces on both sides during the stepping motion to further correct the exerciser's stepping motion. For example, if the foot of the left leg steps on the pedal 12 and turns too much towards the inner side and the foot of the right leg steps on the pedal 12 and turns too much towards the outer side, a message will be prompted to notice the exerciser to make necessary corrections, so that the overturned feet on both left and right sides can be adjusted and corrected. This preferred embodiment can achieve the same effects of the first preferred embodiment including the determination of the abnormal stepping load, the uneven pedaling forces of both feet, and determining whether to stop the stepping motion.

Figure 7:
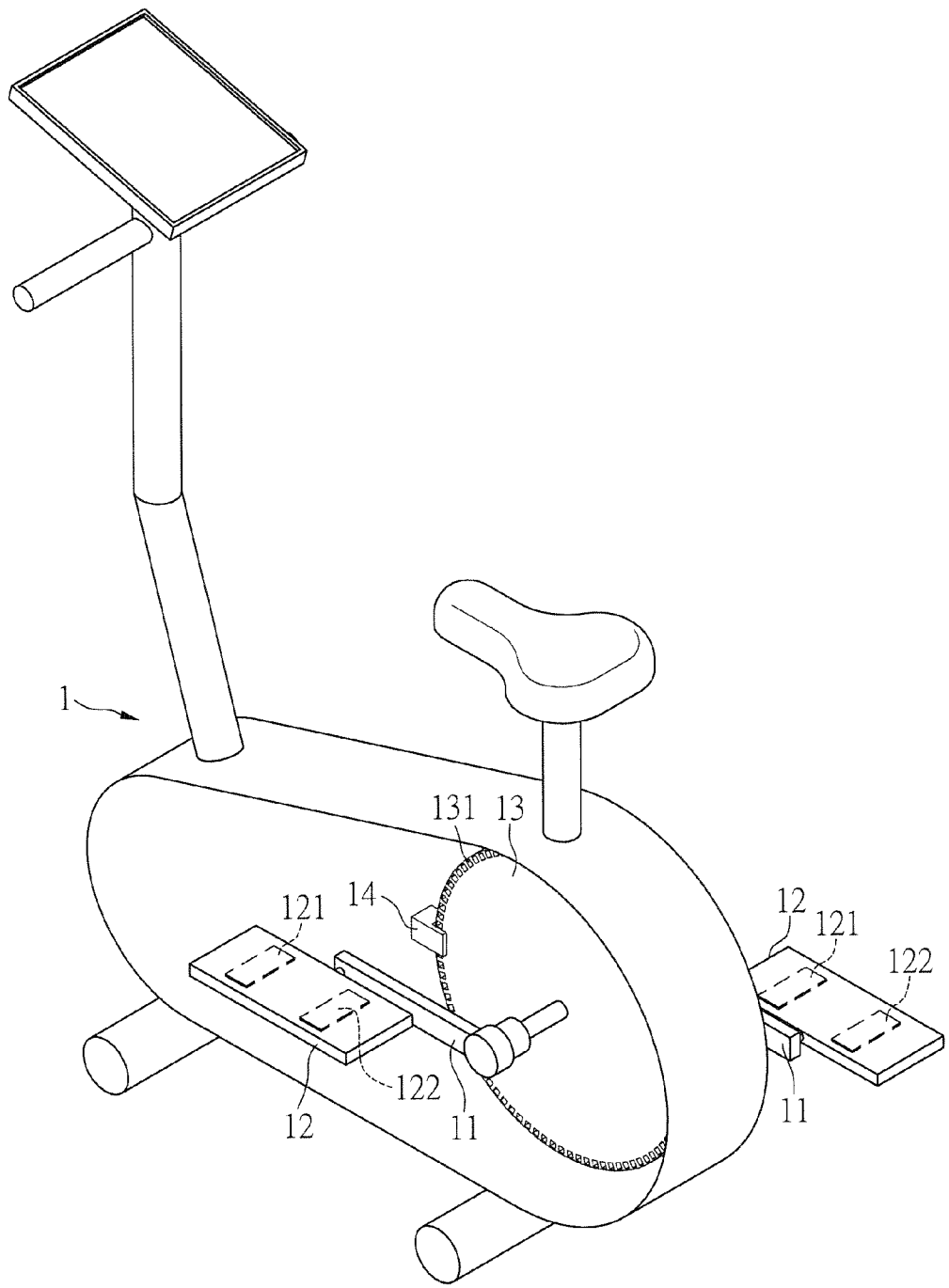
FIG. 7 is a perspective view of a fitness bike in accordance with the third to sixth preferred embodiments of the present invention.
Figure 8:
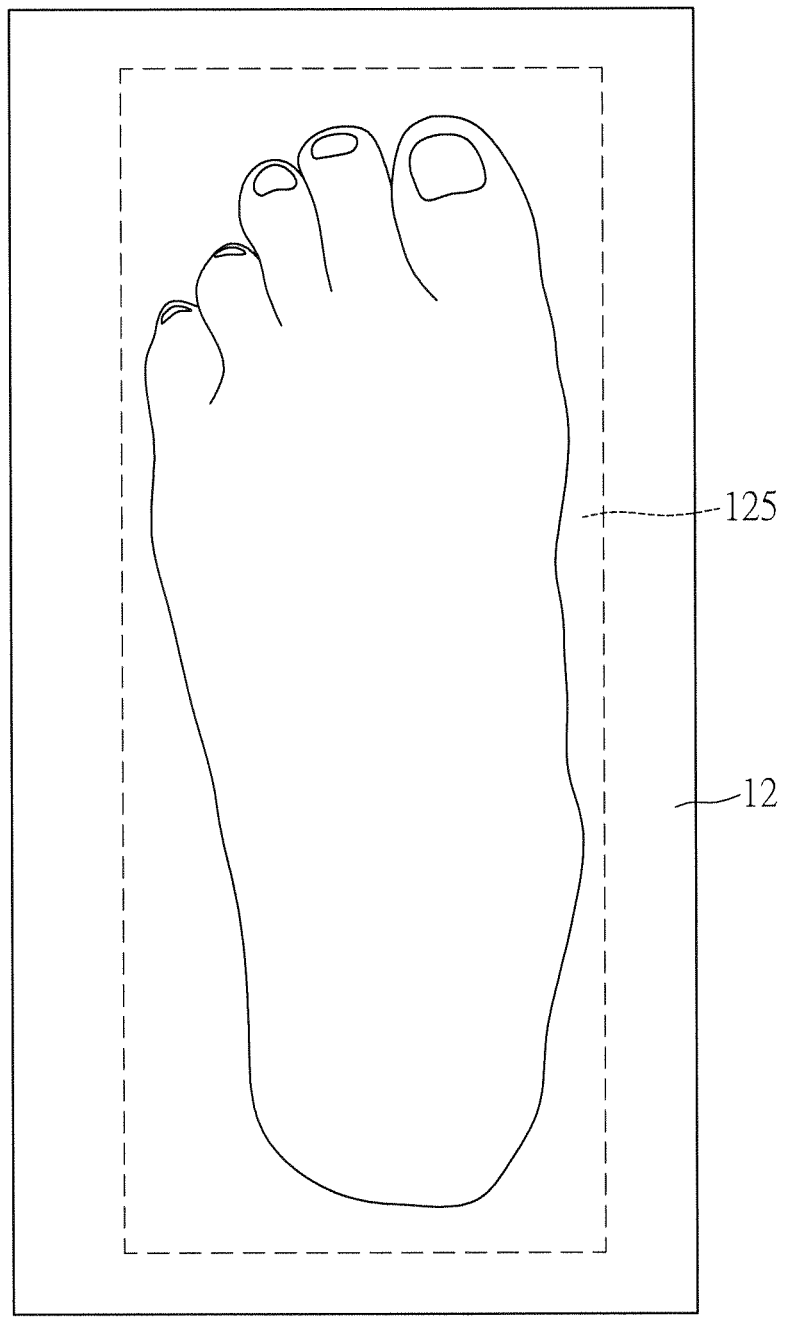
FIG. 8 is schematic view, showing the position of a force sensor installed to a pedal in accordance with the third preferred embodiment of the present invention.
Figure 9:
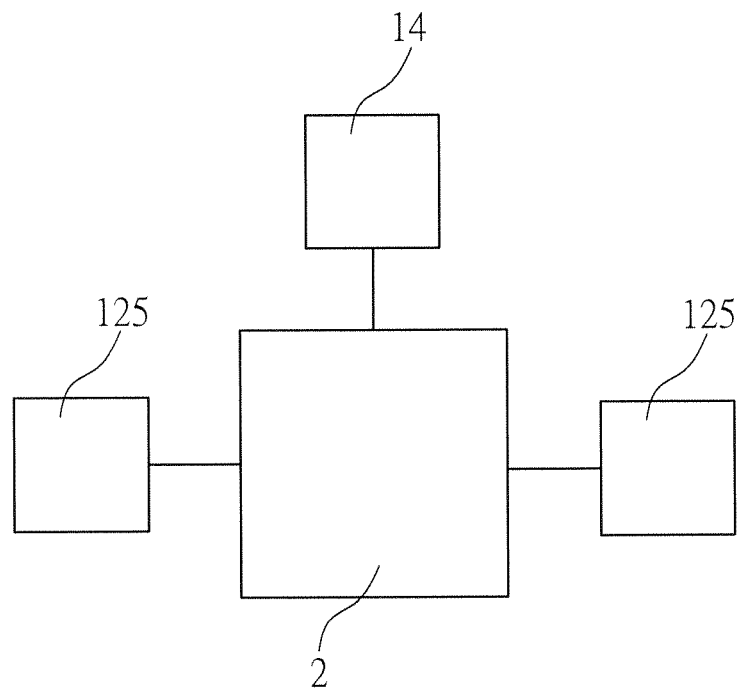
FIG. 9 is a block diagram of a force sensor electrically coupled to a control unit in accordance with the third preferred embodiment of the present invention.

With reference to FIGS. 7 to 10 for the third preferred embodiment of the present invention, the main difference between this preferred embodiment and the previous preferred embodiment resides on that each pedal 12 of the fitness bike 1 as shown in FIG. 7 is coupled to a wheel 13 pivotally installed in an exercise machine by a crank 11, and an angle detector 14 is installed at the wheel 13, and the wheel 13 has a detecting portion 131 corresponsive to the angle detector 14, and the detecting portion 131 of this preferred embodiment is composed of plural grilles which are separately arranged. In FIG. 8, the pedal 12 of this preferred embodiment just includes a force sensor 125. In FIG. 9, the force sensor 125 of each pedal 12 is electrically coupled to the control unit 2.

Figure 10:
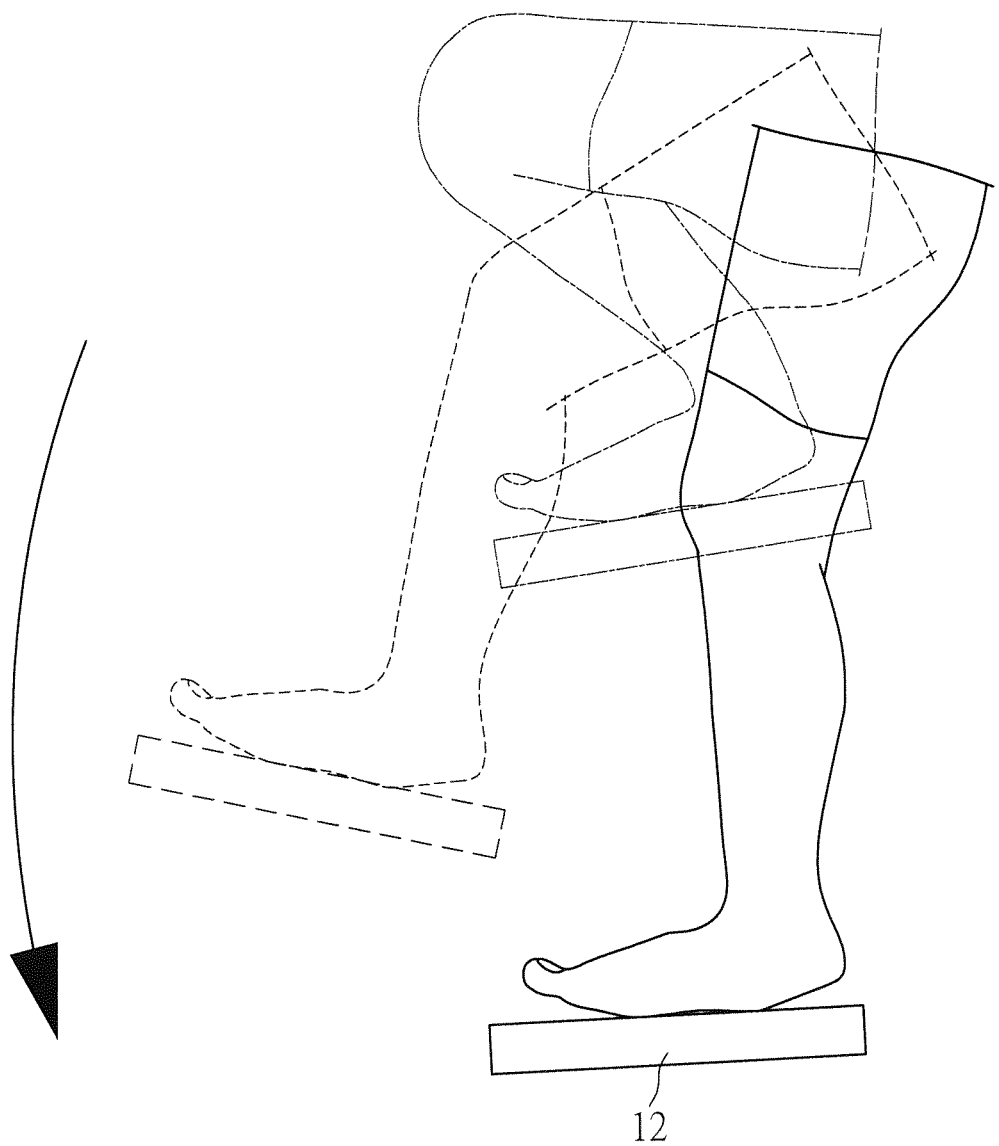
FIG. 10 is a schematic view, showing a lower limb motion when pedals are stepped by an exerciser's feet in accordance with the third preferred embodiment of the present invention.
Figure 11:
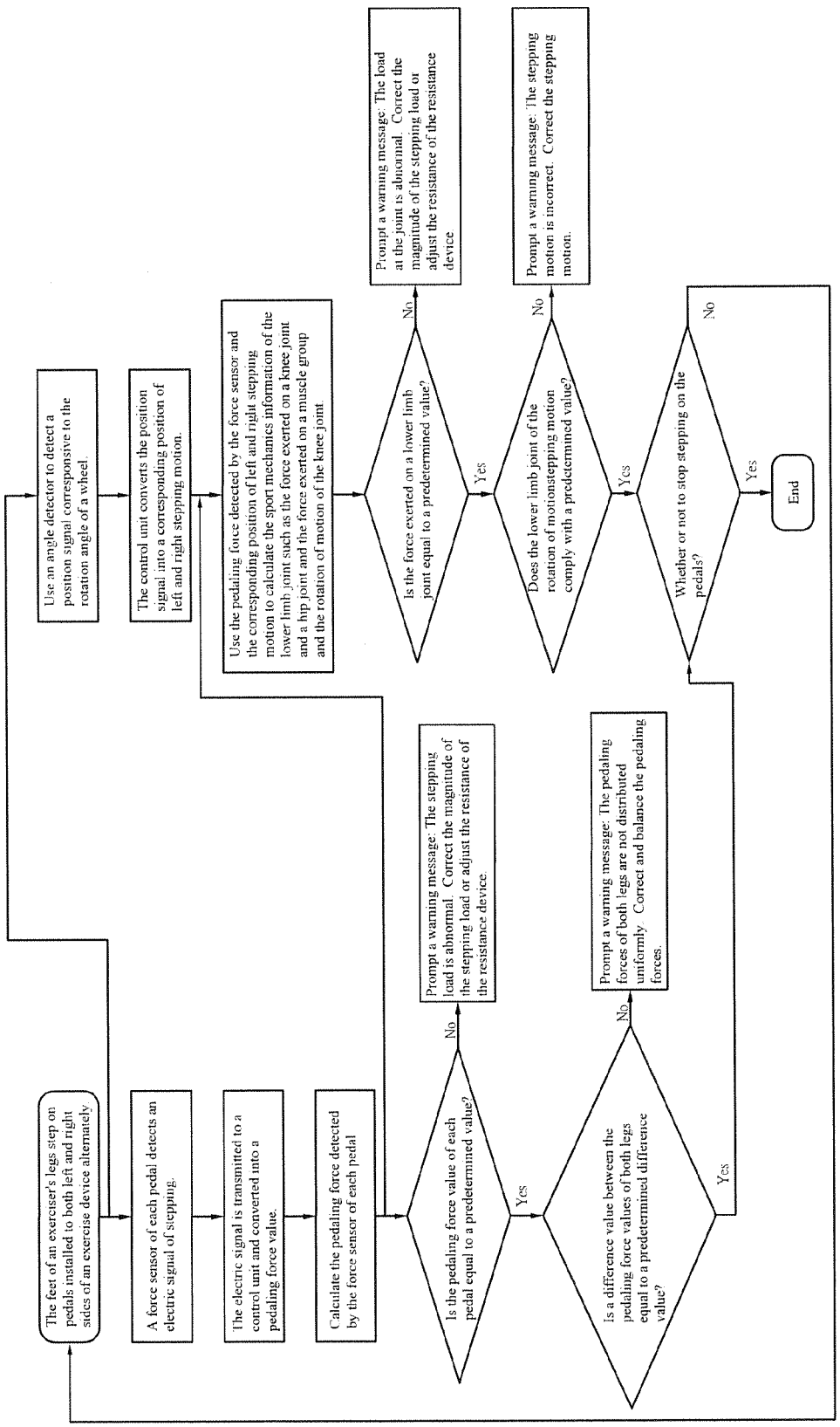
FIG. 11 is a flow chart of detecting and prompting a human lower limbs stepping motion in accordance with the third preferred embodiment of the present invention.

When the exerciser steps on the pedals 12 by the feet to produce a circular motion, the exerciser's lower limbs repeat the contraction and extension as shown in FIG. 10, and the muscles of the lower limbs apply a force to contract and extend the lower limbs, so that the feet produce a pedaling force to the pedal 12. With reference to FIG. 11 for the flow chart of the method of detecting and prompting a human lower limbs stepping motion of this preferred embodiment, the angle detector 14 detects a position signal corresponsive to a rotation angle of the wheel 13, and the control unit 2 calculates the position of the exerciser's foot according to the position signal, and the pedaling force measured by the force sensor 125 which is installed to each pedal 12 is provided for computing the sport mechanics information including the force exerted on the lower limb joint such as a knee joint or a hip joint or a lower limb muscle groups, and a message will be prompted immediately.

In this preferred embodiment, the control unit 2 has a predetermined value stored therein and corresponsive to the force exerted on the lower limb joint. The control unit 2 compares the force exerted on the lower limb joint with to the predetermined value and determine whether it is equal to the predetermined value. If the force exerted on the lower limb joint is not equal to the predetermined value, then a message will be prompted to show the abnormal load of the lower limb joint and let the exerciser correct the magnitude of the pedaling force or adjust the resistance provided by a resistance device. For example, if the exerciser steps on the pedals 12 by the feet of both legs, and the load exerted on the lower limb joint load is too large, then the message will be prompted to notice the exerciser and request the exerciser to reduce the stepping speed or the resistance of the resistance device.

In addition, the control unit 2 of this preferred embodiment has a predetermined value stored in the control unit 2 and corresponsive to the stepping motion of the lower limb joint. The control unit 2 compares the stepping motion of the lower limb joint with a predetermined value corresponsive to the stepping motion of the lower limb joint. If the stepping motion does not comply with the predetermined value, then a message will be prompted to show an abnormal load of the stepping motion load and further correct the stepping motion. For example, if stepping motion of the lower limb joint is too large when the exerciser steps on the pedals 12 by the feet of both legs, a message will be prompted to notice the exerciser and request the exerciser to reduce the stepping motion.

The force sensor 125 of this preferred embodiment can achieve the same effects of the first preferred embodiment and determine the abnormal stepping load and uneven pedaling forces of both feet, and determine whether or not to stop stepping. The angle detector 14 is rotated by the wheel 13 to detect the detecting portion 131, so as to obtain a position signal of the rotation angle. Use the pedaling force detected by the force sensor and the corresponding position of left and right stepping motion to calculate the sport mechanics information of the lower limb joint such as the force exerted on a knee joint and a hip joint and the force exerted on a muscle group and the rotation of motion of the knee joint, so as to achieve the effect of extending the human movement mechanics function.

Figure 12:
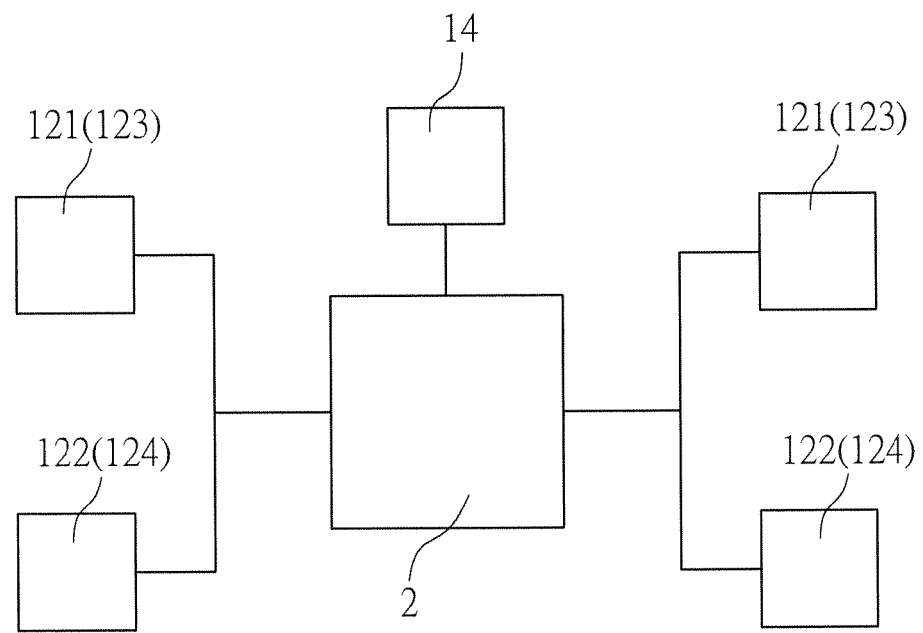
FIG. 12 is a block diagram of a force sensor and an angle detector electrically coupled to a control unit in accordance with the fourth or fifth preferred embodiment of the present invention.
Figure 13:
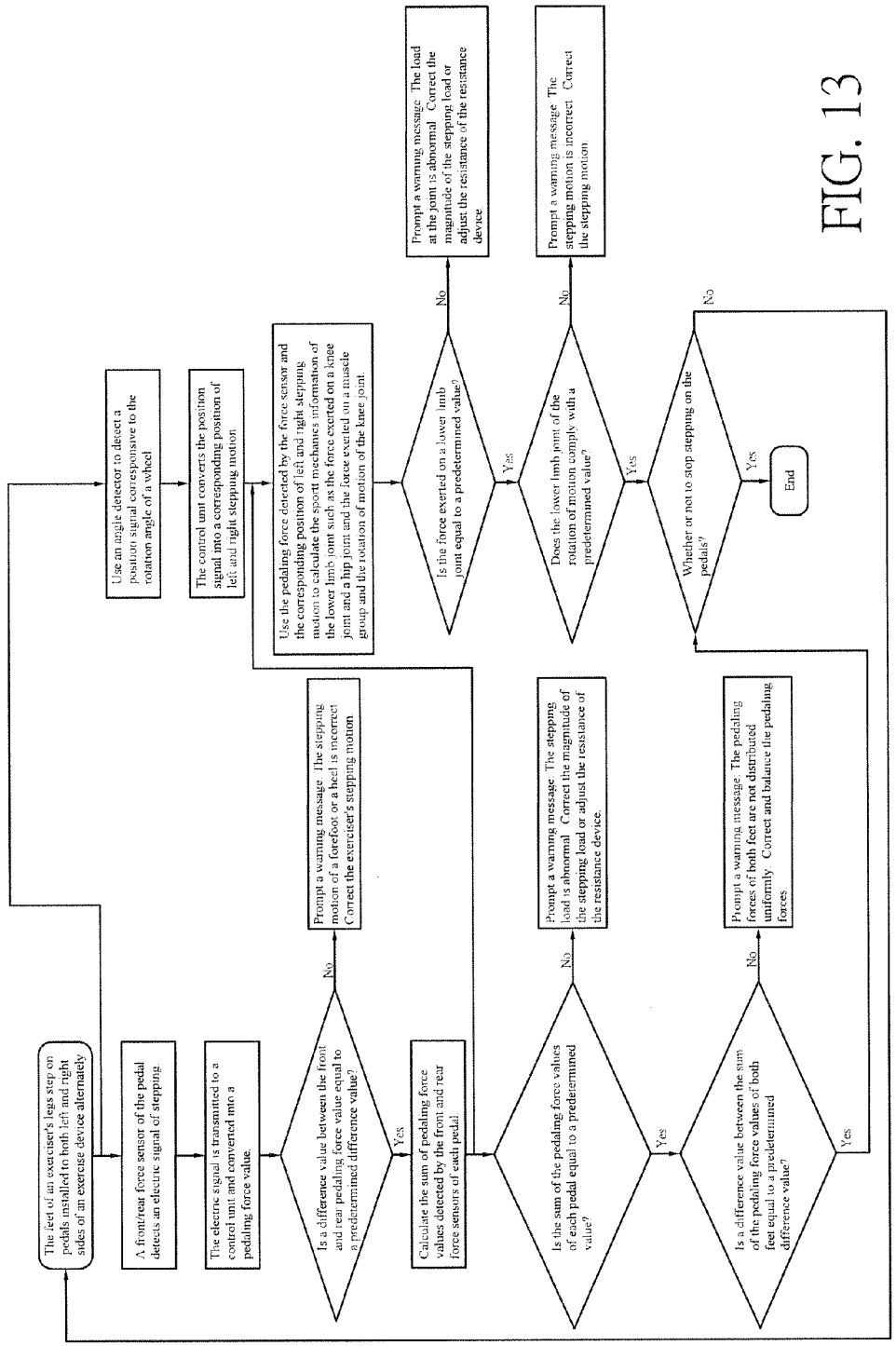
FIG. 13 is a flow chart of detecting and prompting a human lower limbs stepping motion in accordance with the fourth preferred embodiment of the present invention.

With reference to FIGS. 7, 12 and 13 for the fourth preferred embodiment of the present invention, the architecture of the flow of this preferred embodiment is the substantially same as that of the third preferred embodiment, except that the force sensor 125 of this preferred embodiment pedal 12 is changed to that of the first preferred embodiment as shown in FIG. 2. In this preferred embodiment, the pedal 12 includes the front force sensor 121 and the rear force sensor 122 of the first preferred embodiment. As shown in FIG. 12, the front force sensor 121 and the rear force sensor 122 of each pedal 12 are electrically coupled to the control unit 2. As shown in the flow chart as shown in FIG. 13, this preferred embodiment has the same effects of the first preferred embodiment and the third preferred embodiment.

Figure 14:
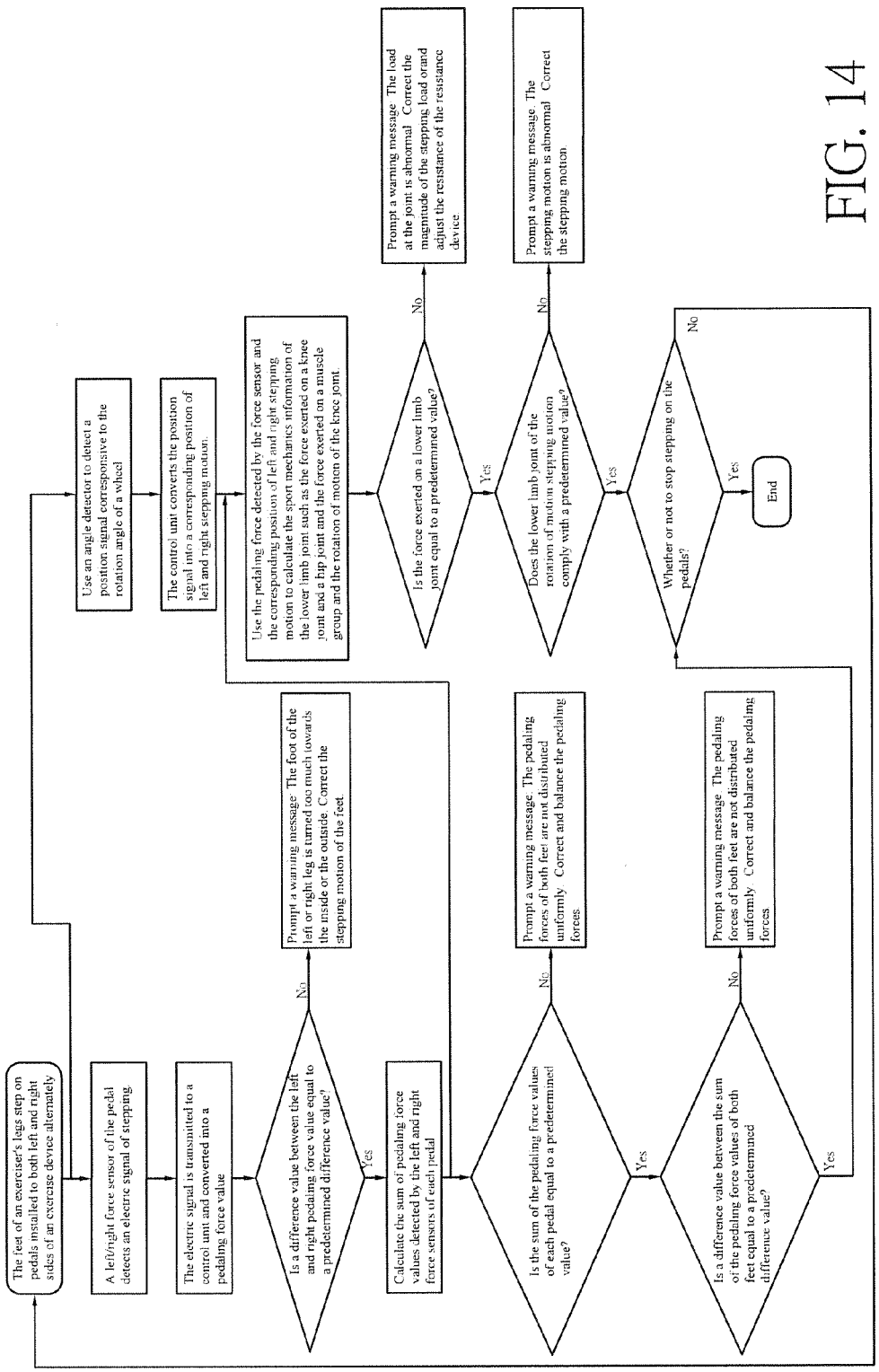
FIG. 14 is a flow chart of detecting and prompting a human lower limbs stepping motion in accordance with the fifth preferred embodiment of the present invention.

With reference to FIGS. 7, 12 and 14 for the fifth preferred embodiment of the present invention, the architecture of the flow of this preferred embodiment is the substantially same as that of the third preferred embodiment, except that the force sensor 125 installed to the pedal 12 of this preferred embodiment is changed to the one similar to that of the second preferred embodiment as shown in FIG. 5, and the pedal 12 of this preferred embodiment further includes the left force sensor 123 and the right force sensor 124 of the second preferred embodiment, and the front force sensor 121 and the rear force sensor 122 of each pedal 12 are electrically coupled to the control unit 2 as shown in FIG. 12. In the flow chart as shown in FIG. 14, this preferred embodiment has the effects of both of the second preferred embodiment and the third preferred embodiment.

Figure 15:
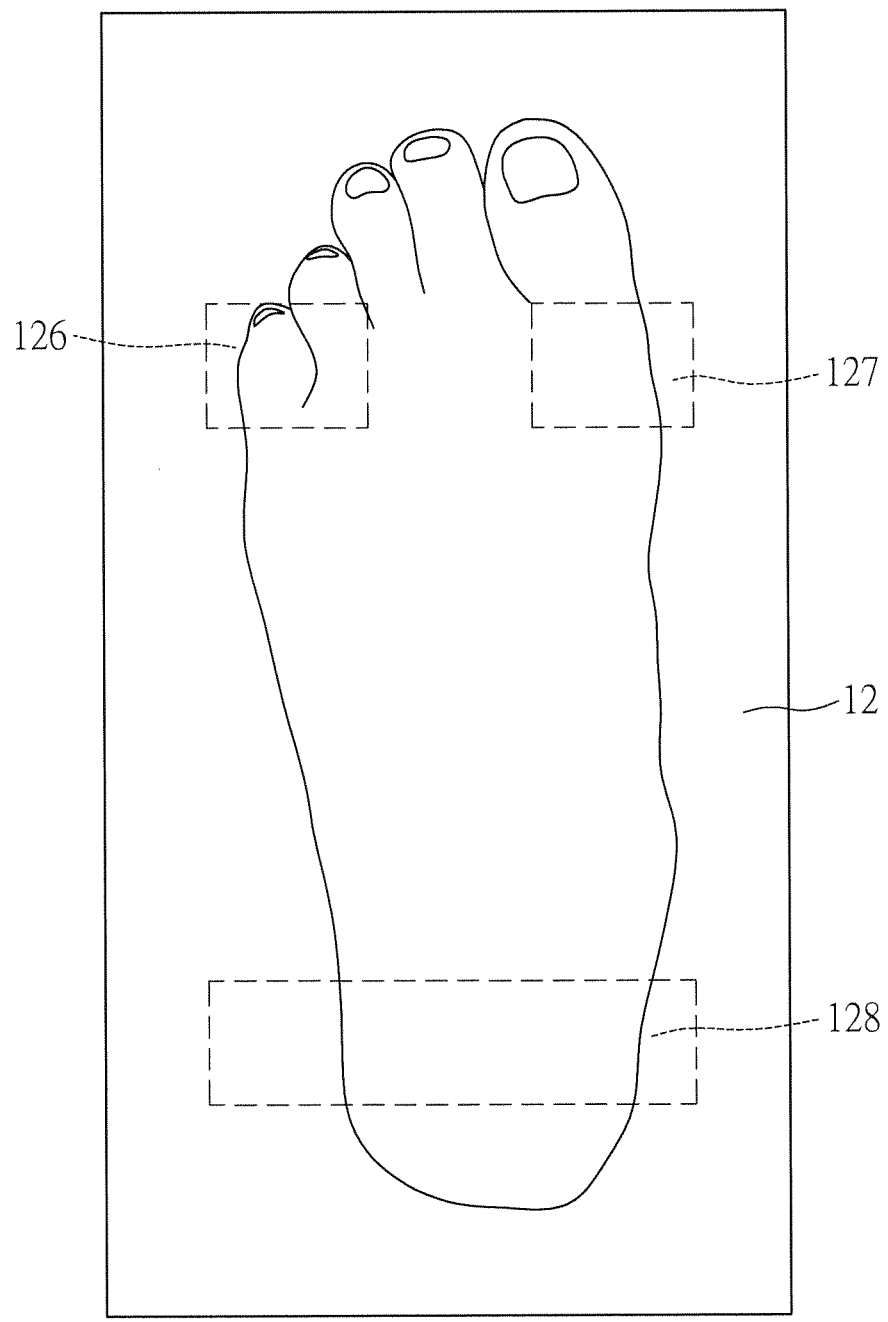
FIG. 15 is a schematic view, showing the position of a force sensor installed to a pedal in accordance with the sixth preferred embodiment of the present invention.
Figure 16:
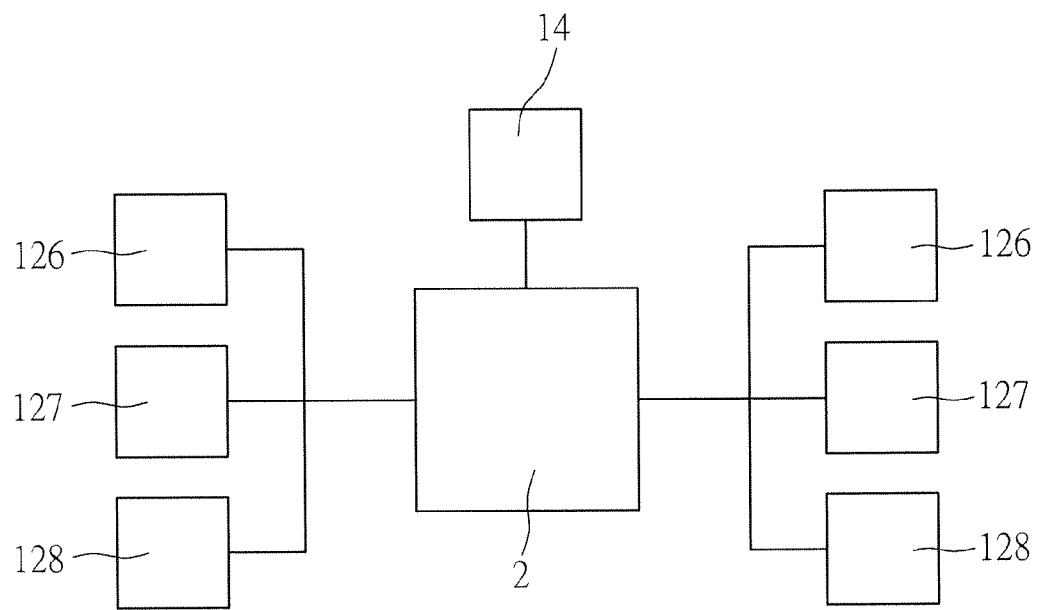
FIG. 16 is a block diagram of a force sensor and an angle detector electrically coupled to a control unit in accordance with the sixth preferred embodiment of the present invention.
Figure 17:
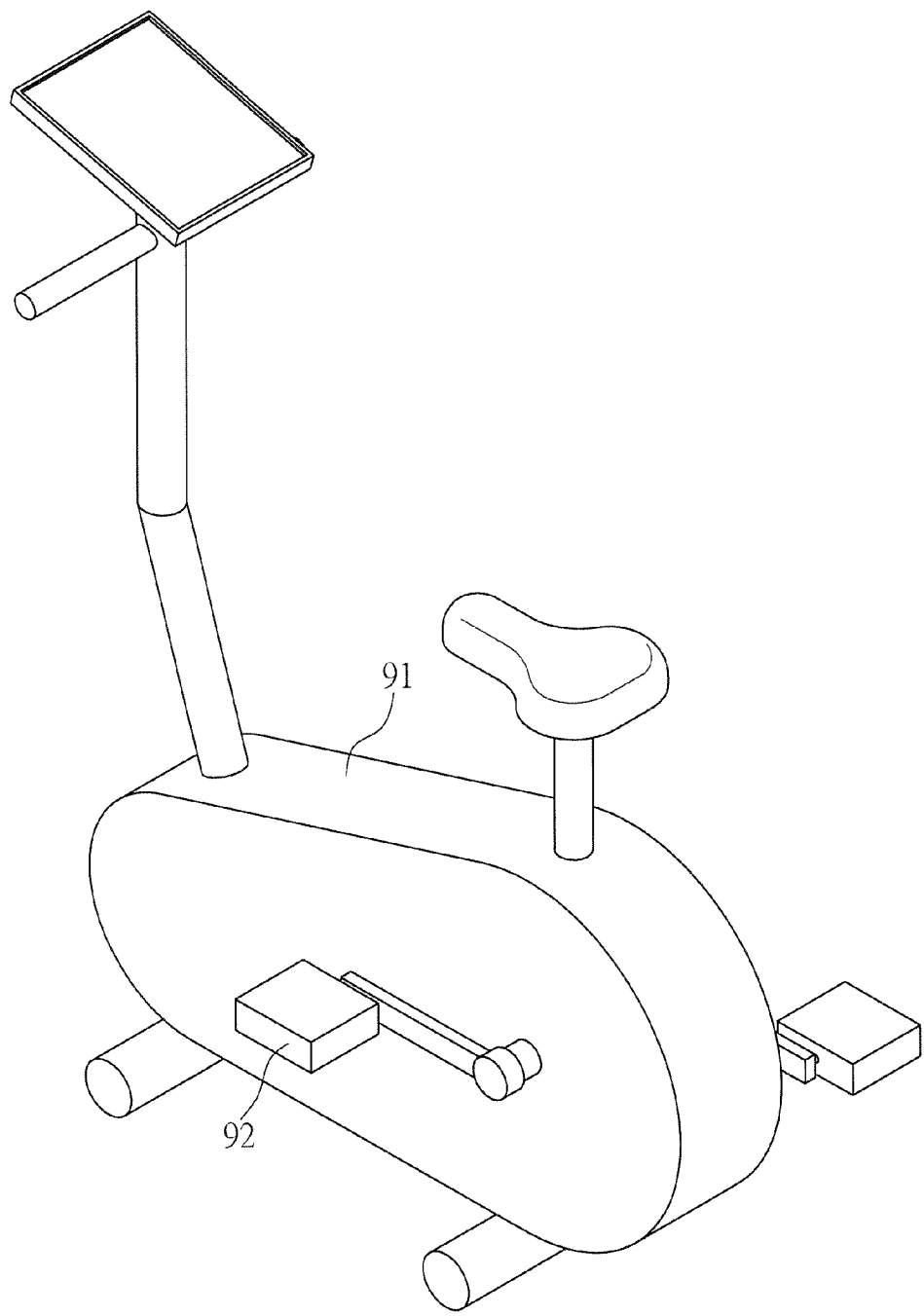
FIG. 17 is a perspective view of a conventional fitness bike.

With reference to FIGS. 7, 15 and 16 for the sixth preferred embodiment of the present invention, the architecture of the flow of this preferred embodiment is the substantially same as that of the third preferred embodiment, except that the force sensor 125 installed to the pedal 12 of this preferred embodiment is changed to the one similar to that of the first preferred embodiment, and there is still a difference from the first preferred embodiment as shown in FIG. 15. In this preferred embodiment, the pedal 12 includes a front force sensor 126, a front force sensor 127 and a rear force sensor 128. As shown in FIG. 16, the front force sensor 126, the front force sensor 127 and the rear force sensor 128 of each pedal 12 are electrically coupled to the control unit 2.

In addition to the effects of the first and third preferred embodiments, this preferred embodiment further comprises two force sensors (including a front force sensor 126 and a front force sensor 127 installed to the front of the pedals 12), and further determines the pedaling forces on the left and right sides when the pedals 12 are stepped by the forefeet of the exerciser's legs, so as to detect the stepping posture and measure the pedaling force of the feet on the pedals 12 more accurately, and the control unit 2 can compare the pedaling force value with the predetermined value more precisely and accurately.

The invention claimed is:

1. A method of detecting and prompting a human lower limbs stepping motion, applied to an exercise machine with pedals installed to both left and right sides of the exercise machine respectively, for detecting a pedaling force when an exerciser steps on the pedals, and the method comprising the steps of:
   installing at least one front force sensor and at least one rear force sensor to each pedal for detecting the pedaling force;
   detecting the pedaling force by the at least one front force sensor and the at least one rear force sensor installed at each pedal to generate at least one electric signal when the feet of the exerciser's legs step on the pedals on both left and right sides of the exercise machine;
   transmitting the at least one electric signal to a control unit and converting the electric signal into a pedaling force value;
   comparing whether the pedaling force value or a difference value of the pedaling force values detected by the at least one front force sensor and the at least one rear force sensor is equal to a predetermined value in the control unit by the control unit; and
   prompting a message if the pedaling force value or the difference value is not equal to the predetermined value;
   wherein each pedal includes the at least one front force sensor installed at the front of the pedal and the at least one rear force sensor installed at the rear of the pedal, and the control unit compares whether the difference value of the pedaling forces detected by the at least one front force sensor and at least one rear force sensor is equal to the predetermined value, and a message is prompted if the difference value is not equal to the predetermined value.

2. The method of detecting and prompting a human lower limbs stepping motion according to claim 1, wherein the pedaling force value is the sum of the pedaling force values detected by the at least one front force sensor and the at least one rear force sensor of each pedal, and the pedaling force value of each pedal is compared with the predetermined value of the control unit to determine whether the sum of the pedaling force values of each pedal is equal to the predetermined value, and a message will be prompted if the sum is not equal to the predetermined value.

3. The method of detecting and prompting a human lower limbs stepping motion according to claim 2, further comprising the steps of:
   calculating a difference value of the sum of the pedaling force values of each pedal by the control unit when the exerciser steps on the two pedals alternately; and
   prompting a message, if the difference value is not equal to the predetermined value.

4. The method of detecting and prompting a human lower limbs stepping motion according to claim 1, wherein each pedal is coupled to a wheel pivotally mounted in the exercise machine, and an angle detector is mounted to the wheel, and the wheel has a detecting portion corresponsive to the angle detector, and an exerciser may step on the pedals reciprocally by the feet, and the angle detector is provided for detecting a position signal of the rotation of the wheel, and the control unit uses the position signal to calculate the position of the exerciser's foot.

5. The method of detecting and prompting a human lower limbs stepping motion according to claim 4, wherein the pedaling force value is the sum of the pedaling force values detected by the at least one front force sensor and the at least one rear force sensor of each pedal, and
the pedaling force value of each pedal is compared with the predetermined value of the control unit to determine whether the sum of the pedaling force values of each pedal is equal to the predetermined value, and a message will be prompted if the sum is not equal to the predetermined value.

6. The method of detecting and prompting a human lower limbs stepping motion according to claim 5, further comprising the steps of:
calculating a difference value of the pedaling forces by the control unit when the two pedals are stepped alternately;
comparing whether the difference value is equal to the predetermined value by the control unit; and
prompting a message if the difference value is not equal to the predetermined value.

7. A method of detecting and prompting a human lower limbs stepping motion, applied to an exercise machine with pedals installed to both left and right sides of the exercise machine respectively, for detecting a pedaling force when an exerciser steps on the pedals, and the method comprising the steps of:
installing at least one left force sensor and at least one right force sensor to each pedal for detecting the pedaling force;
detecting the pedaling force by the at least one left force sensor and the at least one right force sensor installed at each pedal to generate at least one electric signal when the feet of the exerciser's legs step on the pedals on both left and right sides of the exercise machine;
transmitting the at least one electric signal to a control unit and converting the electric signal into a pedaling force value;
comparing whether the pedaling force value or a difference value of the pedaling force values detected by the at least one left force sensor and the at least one right force sensor is equal to a predetermined value in the control unit by the control unit; and
prompting a message if the pedaling force value or the difference value is not equal to the predetermined value;
wherein each pedal includes the at least one left force sensor installed to the left side of the pedal and the at least one right force sensor installed to the right side of the pedal, and the control unit compares whether a difference value of the pedaling force detected by the at least one left force sensor and the at least one right force sensor is equal to the predetermined value, and a message will be prompted if the difference value is not equal to the predetermined value.

8. The method of detecting and prompting a human lower limbs stepping motion according to claim 7, wherein the pedaling force value is the sum of the pedaling force values detected by the at least one left force sensor and the at least one right force sensor of each pedal, and the pedaling force value of each pedal is compared with the predetermined value of the control unit to determine whether the sum of the pedaling force values of each pedal is equal to the predetermined value, and a message will be prompted if the sum is not equal to the predetermined value.

9. The method of detecting and prompting a human lower limbs stepping motion according to claim 8, further comprising the steps of:
calculating a difference value of the sum of the pedaling force values of each pedal by the control unit when the exerciser steps on the two pedals alternately; and
prompting a message, if the difference value is not equal to the predetermined value.

10. The method of detecting and prompting a human lower limbs stepping motion according to claim 7, wherein each pedal is coupled to a wheel pivotally mounted in the exercise machine, and an angle detector is mounted to the wheel, and the wheel has a detecting portion corresponsive to the angle detector, and an exerciser may step on the pedals reciprocally by the feet, and the angle detector is provided for detecting a position signal of the rotation of the wheel, and the control unit uses the position signal to calculate the position of the exerciser's foot.

11. The method of detecting and prompting a human lower limbs stepping motion according to claim 10, wherein the pedaling force value is the sum of the pedaling force values detected by the at least one left force sensor and the at least one right force sensor of each pedal, and
the pedaling force value of each pedal is compared with the predetermined value of the control unit to determine whether the sum of the pedaling force values of each pedal is equal to the predetermined value, and a message will be prompted if the sum is not equal to the predetermined value.

12. The method of detecting and prompting a human lower limbs stepping motion according to claim 11, further comprising the steps of:
calculating a difference value of the pedaling forces by the control unit when the two pedals are stepped alternately;
comparing whether the difference value is equal to the predetermined value by the control unit; and
prompting a message if the difference value is not equal to the predetermined value.

13. A method of detecting and prompting a human lower limbs stepping motion, applied to an exercise machine with pedals installed to both left and right sides of the exercise machine respectively, for detecting a pedaling force when an exerciser steps on the pedals, and the method comprising the steps of:
installing at least one force sensor to each pedal for detecting the pedaling force;
detecting the pedaling force by the at least one force sensor installed at each pedal to generate at least one electric signal when the feet of the exerciser's legs step on the pedals on both left and right sides of the exercise machine;
transmitting the at least one electric signal to a control unit and converting the electric signal into a pedaling force value;
comparing whether the pedaling force value or a difference value of the pedaling force values detected by the at least one force sensor is equal to a predetermined value in the control unit by the control unit; and
prompting a message if the pedaling force value or the difference value is not equal to the predetermined value;

wherein each pedal is coupled to a wheel pivotally mounted in the exercise machine, and an angle detector is mounted to the wheel, and the wheel has a detecting portion corresponsive to the angle detector, and an exerciser may step on the pedals reciprocally by the feet, and the angle detector is provided for detecting a position signal of the rotation of the wheel, and the control unit uses the position signal to calculate the position of the exerciser's foot.

14. The method of detecting and prompting a human lower limbs stepping motion according to claim 13, wherein the pedaling force value is the sum of the pedaling force values detected by the at least one force sensor of each pedal, and the pedaling force value of each pedal is compared with the predetermined value of the control unit to determine whether the sum of the pedaling force values of each pedal is equal to the predetermined value, and a message will be prompted if the sum is not equal to the predetermined value.

15. The method of detecting and prompting a human lower limbs stepping motion according to claim 14, further comprising the steps of:
    calculating a difference value of the sum of the pedaling force values of each pedal by the control unit when the exerciser steps on the two pedals alternately; and
    prompting a message, if the difference value is not equal to the predetermined value.

16. The method of detecting and prompting a human lower limbs stepping motion according to claim 13, wherein the pedaling force value is the sum of the pedaling force values detected by the at least one force sensor of each pedal, and
    the pedaling force value of each pedal is compared with the predetermined value of the control unit to determine whether the sum of the pedaling force values of each pedal is equal to the predetermined value, and a message will be prompted if the sum is not equal to the predetermined value.

17. The method of detecting and prompting a human lower limbs stepping motion according to claim 16, further comprising the steps of:
    calculating a difference value of the pedaling forces by the control unit when the two pedals are stepped alternately;
    comparing whether the difference value is equal to the predetermined value by the control unit; and
    prompting a message if the difference value is not equal to the predetermined value.

* * * * *